United States Patent [19]

Fujita et al.

[11] 3,975,451

[45] Aug. 17, 1976

[54] DIOLS AND PROCESS FOR PREPARATION THEREOF

[75] Inventors: Yoshiji Fujita; Takashi Nishida; Kazuo Itoi, all of Kurashiki, Japan

[73] Assignee: Kuraray Co., Ltd., Kurashiki, Japan

[22] Filed: May 30, 1975

[21] Appl. No.: 582,399

[30] Foreign Application Priority Data

May 30, 1974 Japan............................. 49-61204

[52] U.S. Cl..................... 260/635 Y; 260/632 R; 260/632 Y; 260/635 R; 260/635 M; 260/638 Y; 260/682

[51] Int. Cl.²........................................ C07C 33/04

[58] Field of Search............................ 260/635 Y

[56] References Cited

UNITED STATES PATENTS

| | | | |
|---|---|---|---|
| 2,525,672 | 10/1950 | Heilbron et al.............. | 260/635 Y |
| 2,809,216 | 10/1957 | Inhoffen et al.............. | 260/635 Y |
| 2,952,718 | 9/1960 | Kauer........................... | 260/635 Y |
| 3,065,283 | 11/1962 | Happel et al................. | 260/635 Y |

OTHER PUBLICATIONS

Singer et al, "J. Chem. Soc." (A), 1968, pp. 849–853.
Weichet et al, "Chem. Abstracts", vol. 52 (1953), col. 10989f.

*Primary Examiner*—Joseph E. Evans
*Attorney, Agent, or Firm*—Bacon & Thomas

[57] ABSTRACT

An alkyne-10,15-diol is synthesized by coupling a 3-alkynol containing methyl groups by using as a catalyst a complex comprised of a halide of a metal of Group VII of the Periodic Table coordinated with an organic phosphorus compound.

The so-obtained diol can be formed into squalane [2,6,10,15,19,23-hexamethyl tetracosane] by hydrogenolysis, a combination of hydrogenation and hydrogenolysis or a combination of hydrogenation, dehydration and hydrogenation.

3 Claims, No Drawings

DIOLS AND PROCESS FOR PREPARATION THEREOF

BACKGROUND OF THE INVENTION

The present invention relates to novel unsaturated diols, a process for preparing same and a process for converting these diols to squalane.

It is well known that a diacetylene diol is prepared by subjecting an alkynol to the oxidative coupling reaction in an oxygen atmosphere in the presence of a copper-pyridine complex as a catalyst to dimerize the alkynol (J. Chem. Soc., 1974, pages 1579–1583).

The present inventors have previously described a process for synthesizing squalane which comprises subjecting an alkynol represented by the following general formula [II]:

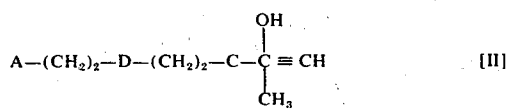

[II]

wherein A and D are as defined above in the general formula [I], to an oxidative coupling reaction in an oxygen atmosphere in the presence of a known coupling catalyst, namely a copper-pyridine complex compound, to form a diacetylene dialcohol repesented by the following general formula:

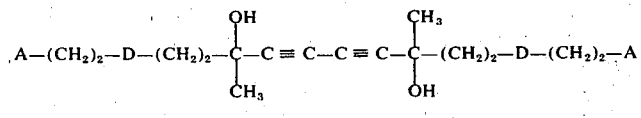

wherein A and D are as defined above in the general formula [I], and subjecting the diacetylene dialcohol to hydrogenolysis or a combination of hydrogenation, dehydration and hydrogenation (British Patent Applications Nos. 11465/74 and 14126/74; United States patent application Ser. Nos. 448,700 and 454,694.

However, it has been found that desirable repeated use of the copper-pyridine complex compound as a catalyst is very difficult as a consequence of the problems encountered in separating and recovering the catalyst from the reaction system and because the activity of the catalyst is lowered. Further, reaction of a triple bond-containing compound such as an alkynol in a reaction system including a heavy metal compound such as copper-pyridine and oxygen always involves a danger of sympathetic detonation.

SUMMARY OF THE INVENTION

Accordingly, it is a primary object of the present invention to afford a process in which the catalyst can easily be recovered and used repeatedly and wherein it is possible to adopt reaction conditions much milder than known oxidative coupling conditions. Further, since oxygen is not used, the danger involved in effectuating the reaction is considerably reduced compared to known oxidative coupling methods.

It is a further object of this invention to provide alkyne-10,15-diols represented by the general formula [I] hereinbelow (hereinafter referred to as "diol [I]"), which is a useful intermediate and from which squalane can be easily synthesized by hydrogenolysis or a combination of dehydration and hydrogenation.

Other objects, features and advantages of this invention will become more apparent to those skilled in the art from the detailed description of the invention which follows.

DETAILED DESCRIPTION OF THE INVENTION

This invention relates to a diol of an unsaturated hydrocarbon having in the molecule one triple bond and 1 to 5 double bonds, a process for preparing same and a process for preparing squalane from the aforesaid diol.

The diol of this invention has a structure represented by the following general formula [I]:

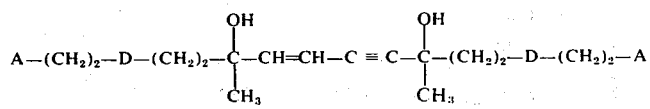

wherein A is

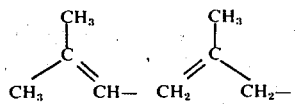

or

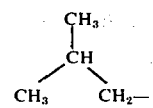

D is

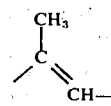

or

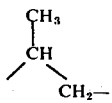

and wherein the A— groups may be the same or different and the —D— groups may be the same or different.

As unsaturated hydrocarbon diols of the above formula having one triple bond and 1 to 5 double bonds, one of which forms a conjugated bond with the triple bond, there may be mentioned 2,6,10,15,19,23-hexamethyltetracosa-11-yne-E-10,15-diol which includes the following 36 compounds:

a. Where E is mono-en, the following one compound is mentioned:
 -13-enb. Where E is di-en, the following six compounds are mentioned:
 -1,13-dien-
 -2,13-dien-
 -6,13-dien-
 -13,18-dien-
 -13,22-dien-
 -13,23-dienc. Where E is tri-en, the following 13 compounds are mentioned:
 -1,6,13-trien-
 -1,13,18-trien-
 -1,13,22-trien-
 -1,13,23-trien-
 -2,6,13-trien-
 -2,13,18-trien-
 -2,13,22-trien-
 -2,13,23-trien-
 -3,18,23-trien-
 -6,13-18-trien-
 -6,13,22-trien-
 -6,13,23-trien-
 -13,18,22-triend. Where E is tetra-en, the following 12 compounds are mentioned:
 -1,6,13,18-tetraen-
 -1,6,13,22-tetraen-
 -1,6,13,23-tetraen-
 -1,13,18,22-tetraen-
 -1,13,18,23-tetraen-
 -2,6,13,18-tetraen-
 -2,6,13,22-tetraen-
 -2,6,13,23-tetraen-
 -2,13,18,22-tetraen-
 -2,13,18,23-tetraen-
 -6,13,18,22-tetraen-
 -6,13,18,23-tetraene. Where E is penta-en, the following 4 compounds are mentioned:
 -1,6,13,18,22-pentaen-
 -1,6,13,18,23-pentaen-
 -2,6,13,18,22-pentaen-
 -2,6,18,23-pentaen- I. Synthesis of Diol [I]:

The diol [I] of this invention can be prepared in a good yield according to the following process.

More specifically, the diol [I] is prepared by reacting at least one alkynyl alcohol represented by the following general formula [II]

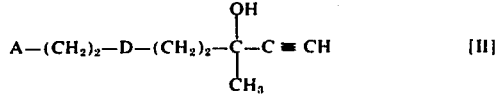

$$A-(CH_2)_2-D-(CH_2)_2-\underset{\underset{CH_3}{|}}{\overset{\overset{OH}{|}}{C}}-C\equiv CH \quad [II]$$

wherein A and D are as defined above in the general formula [I], in the presence of a compound represented by the following general formula [III]:

$$MX_m(Lig)_n \quad [III]$$

wherein M is a metal of Group VIII of the Periodic Table, X is a halogen atom, Lig designates a liquid such as $(C_6H_5)PO$, $(C_6H_5)_3P$, $(C_6H_5O)_3P$, $(cycloalkyl)_3P$ or $(alkyl)_3P$, and $m$ and $n$ are integers of 1 to 3, as a catalyst to dimerize the alkynyl alcohol.

As the alkynyl alcohol represented by the general formula [II], any of the following compounds may be utilized:
 3,7,11-trimetyldodeca-1-yne-6,10-dien-3-ol,
 3,7,11-trimethyldodeca-1-yne-6,11-dien-3-ol,
 3,7,11-trimethyldodeca-1-yn-6-en-3-ol,
 3,7,11-trimethyldodeca-1-yn-10-en-3-ol,
 3,7,11-trimethyldodeca-1-yn-11-en-3-ol, and
 3,7,11-trimethyldodeca-1-yn-3-ol.

The foregoing alkynyl alcohols can easily be prepared by any of the following methods.

3,7,11-trimethyldodeca-1-yne-6,10-dien-3-ol can be synthesized by reacting linalool, which is synthesized on an industrial scale as a perfume, with ethyl acetoacetate or diketene, subjecting the resulting reaction product to Caroll rearrangement in the presence of a catalyst such as an alkyl aluminum to form geranyl acetone, and subjecting geranyl acetone to ethynylation in the presence of a catalyst, such as metallic sodium or metal alkoxide in liquid ammonia.

3,7,11-trimethyldodeca-1-yne-6,11-dien-3-ol can be obtained by halogenating 3-methyl-3-buten-1-ol, which is formed as a by-product in isoprene synthesis with phosphorus trichloride or phosphorus tribromide, reacting the halogenation product with ethyl acetoacetate to form 6-methyl-6-hepten-2-one, subjecting 6-methyl-6-hepten-2-one to ethynylation in the same manner as described above, thereafter subjecting the ethynylation product to partial hydrogenation in the presence of a Lindler catalyst, subjecting the partial hydrogenation product to Caroll rearrangement by using ethyl acetoacetate or diketene, and subjecting the rearrangement product to ethynylation.

3,7,11-trimethyldodeca-1-yn-5-en-3-ol can be synthesized by hydrogenating heptaene or 6-methyl-6-hepten-2-one in the presence of a Pd/C catalyst and conducting ethynylation, partial hydrogenation, Caroll rearrangement and ethynylation in the same manner as described above.

3,7,11-trimethyldodeca-1-yn-10-en-3-ol can easily be synthesized by halogenating citronellol, which is used as a perfume, with phosphorus trichloride or phosphorus tribromide, reacting the halogenation product with ethyl acetoacetate to form 6,10-dimethylundeca-9-en-2-one, and subjecting it to ethynylation in the same manner as described above.

It is difficult to synthesize 3,7,11-trimethyldodeca-1-yn-11-en-3-ol of high purity. When hydroxycitronellal, which is used as a perfume, is subjected to Aldol condensation together with acetone, the condensation product is hydrogenated in the presence of a Pd/C catalyst and the hydrogenation product is dehydrated with sulfuric acid or the like, there is obtained a mixture of 6,10-dimethylundeca-9-en-2-one and 6,10-dimethylundeca-10-en-2-one. When this mixture is subjected to ethynylation in the same manner as described above, there is formed a mixture of 3,7,11-trimethyldodeca-1-yn-10-en-3-ol and 3,7,11-trimethyldodeca-1-yn-11-en-3-ol.

When any of the above compounds is used, all the unsaturated bonds are converted to saturated bonds after the coupling reaction. Therefore, each of these compounds can be used as an intermediate leading to squalane conveniently.

The catalyst to be used for the coupling reaction of the alkynol in this invention is described immediately below.

In the compound represented by the above general formula [III], M is a metal of the Group VIII of the Periodic Table, namely a metal selected from Fe, Co, Ni, Ru, Rh, Pd, Os, Ir and Pt. Compounds of the general formula [III] in which the metal M is selected from Co, Ni, Ru, Rh, Pd and Pt are especially preferred.

In the general formula [III], X represents a halogen atom selected from Cl, Br and I.

In the general formula [III], Lig stands for a ligand (coordination compound) such as $(C_6H_5)_3PO$, $(C_6H_5)_3PO$, $(C_6H_5)_3P$, (cycloalkyl)$_3P$ and (alkyl)$_3P$. The cycloalkyl group includes cycloalkyl groups having 3 to 10 carbon atoms, and the alkyl group includes alkyl groups having 1 to 20 carbon atoms. More specifically, as the alkyl group, methyl, ethyl, n-propyl, isopropyl, n-butyl, isobutyl, tert-butyl, pentyl, heptyl, hexyl, octyl, nonyl and stearyl groups may be mentioned; and as the cycloalkyl group, there may be mentioned a cyclohexyl group. Each of $m$ and $n$ is an integer of from 1 to 3.

As specific examples of the catalyst compound represented by the general formula [III], the following compounds are mentioned:

$RhCl[P(C_6H_5)_3]_3$,
$PdCl_2[P(C_6H_5)_3]_2$,
$PtCl_2[P(C_6H_5)_3]_2$,
$PtCl_2[P(OC_6H_5)_3]_2$,
$CoCl_2[P(C_6H_5)_3]_2$,
$CoBr_2[P(C_6H_5)_3]_2$,
$CoI_2[P(C_6H_5)_3]_2$,
$CoBr_2[P(cyclohexyl)_3]_2$,
$CoI_2[P(cyclohexyl)_3]_2$,
$NiCl_2[P(C_6H_5)_3]_2$,
$NiBr_2[P(C_6H_5)_3]_2$,
$NiI_2[P(C_6H_5)_3]_2$, and
$RuCl_2[P(C_6H_5)_3]_3$.

When the process of this invention is carried out, the reaction reported by G. Wilkinson et al in *J. Chem. Soc.*, (A), 849–853 (1968) can be utilized.

This reaction can be accomplished by heating a compound represented by the general formula [II] in the presence of a catalyst represented by the general formula [III] in an amount of at least 0.1% by weight based on the compound of the general formula [II] in a suitable solvent, and, preferably, in an atmosphere of an inert gas such as $N_2$ and argon.

The reaction can be performed at a temperature ranging from room temperature (about 25°C.) to 200°C., but it is preferred that the reaction be carried out at approximately 80° to 150°C. As the reaction solvent, there can be used solvents that are not substantially altered under the reaction conditions of the process. For example, aromatic hydrocarbons, such as benzene, toluene and xylene, aliphatic hydrocarbons such as cyclohexane, ethylcyclohexane and ligroin, amides such as dimethylformamide, alcohols such as ethanol, isopropanol and octanol, ethers such as tetrahydrofuran, ethyl ether and dioxane, nitriles such as acetonitrile and propionitrile, and carbonyl compounds such as acetone and methylethylketone may be utilized.

II. Synthesis of Squalane from Diol [I]:

Squalane can be readily synthesized from the diol [I] obtained according to the above-mentioned process, by the following methods.

i. The diol [I] is hydrogenated to obtain 2,6,10,15,19,23-hexamethyltetracosa-10,15-diol, and the so formed compound is subjected to dehydration with a dehydrating agent as disclosed in the specification of British Patent Application No. 14126/74, and U.S. patent application Ser. No. 454,694. incorporated by reference herein, to thereby form an unsaturated compound free of a hydroxyl group. Then, the obtained unsaturated compound is subjected to hydrogenation to obtain squalane.

ii. The diol [I] is converted to 2,6,10,15,19,23-hexamethyltetracosa-10,15-diol by hydrogenation as in the method (i), and the so formed compound is subjected to hydrogenolysis as disclosed in the specification of British Patent Application No. 11465/74 and U.S. patent application Ser. No. 448,700.

iii. The diol [I] is subjected to partial hydrogenation to hydrogenate preferentially the triple bond of the diol [I] and convert same to a diol having double bonds but being free of a triple bond, and this diol is converted to squalane by hydrogenolysis.

iv. The diol [I] is converted directly to squalane by hydrogenolysis.

[A] Ordinary hydrogenation reactions can be adopted in the above methods (i), (ii) and (iii) for synthesizing squalane from the diol [I].

As the hydrogenation catalyst, there may be employed, for example, Ni, Co, Pd, Pt, Rh, Ir, Ru and Os. Among these catalysts, Raney nickel, nickel supported on a carrier such as diatomaceous earth (hereinafter abbreviated "Ni-diatomaceous earth" or the like) and palladium supported on active carbon are ordinarily employed.

Under some reaction conditions, hydrogenolysis is carried out concurrently with hydrogenation, and 2,6,10,15,19,23-hexamethyltetracosan-10-ol or squalane is formed as a byproduct and a mixture of such by-product and the intended 2,6,10,15,19,23-hexamethyltetracosa-10,15-diol is obtained as the reaction product. This mixture, however, can be fed directly to the next step. In order to obtain the 10,15-diol alone, it is prefered that a Raney catalyst such as Raney nickel or Raney cobalt be used as the hydrogenation catalyst.

It is not preferred to use acidic or highly polar solvents as the reaction solvent. Saturated hydrocarbons, saturated ethers and saturated esters which do not change under the hydrogenation reactions are generally employed.

The hydrogenation reaction is influenced by the reaction temperature, and the reaction is generally conducted at low temperatures. It is especially preferred that the hydrogenation be carried out at a temperature of about 50° to about 150°C.

The partial hydrogenation of the diol [I] for obtaining an unsaturated diol free of a triple bond in the method (iii) is performed under milder conditions than in the above-mentioned hydrogenation reaction.

In general, the triple bond is hydrogenated most readily, and di-substituted olefins are more readily hydrogenated than tri-substituted olefins.

If diol [I] is hydrogenated under severe conditions or under such conditions as will readily cause hydrogenolysis, cyclization often occurs and squalane of high purity is not obtained. It has been discovered that such undesired side reaction is avoided when, as in the above method (iii), the triple bond of the diol [I] is first hydrogenated and the resulting unsaturaed diol (partial hydrogenation product) is then subjected to hydrogenolysis.

Under the preceding hydrogenolysis conditions, unsaturated bonds of the unsaturated diol are readily hydrogenated. Therefore, it is unnecessary to hydrogenate all the unsaturated bonds in the hydrogenation step of the starting diol [I].

The hydrogenation catalysts mentioned above can also be used for this partial hydrogenation, but especially good results are obtained when catalysts having a high degree of activity, even under mild temperature conditions, such as Raney nickel and Pd supported active carbon (Pd-C catalyst), are employed. Moreover, use of these catalysts is preferred from an economical viewpoint. It is preferred that the reaction be carried out at a temperature ranging from room temperature to about 100°C.

When an unsaturated compound free of hydroxyl groups obtained by hydrogenating the diol [I] and subjecting the hydrogenation product to dehydration is hydrogenated again in the above-mentioned method (i), the hydrogenation can be performed under the same conditions as described above.

In each of the foregoing hydrogenation reactions, the hydrogen pressure need not be above 150 Kg/cm$^2$, and the reaction proceeds even under atmospheric hydrogen pressure.

Diols [I] and the above-mentioned hydrogenation products thereof are highly viscous. Accordingly, it is preferred that the hydrogenation reaction be carried out in a suitable solvent. Saturated hydrocarbons, ethers, alcohols and esters are preferably used as such solvents.

[B] The following reaction conditions are adopted for dehydrating the hydrogenation product of the diol [I] in the above-mentioned method (i).

The following catalysts are used for this dehydration:

a. Brønsted acids such as sulfuric acid, hydrochloric acid, phosphoric acid, perchloric acid, boric acid and the like;

b. Lewis acids such as zinc chloride, aluminum chloride, boron trifluoride, tin tetrachloride and the like;

c. Acidic salts of strong acids and strong bases such as sodium hydrogensulfate, sodium hydrogenphosphate, potassium hydrogensulfate and the like;

d. Salts of strong acids and weak bases such as magnesium sulfate, zinc sulfate, calcium sulfate, copper sulfate, magnesium chloride, and the like; and e. Solid acids such as silica-alumina, alumina, solid phosphoric acid, cation exchange resins and the like.

The reaction is carried out in the presence of such catalyst in the absence of a solvent or in the presence of a suitable solvent in which the hydrogenation product of the diol [I] is dissolved. For example, when a mineral acid such as sulfuric acid and phosphoric acid, a Lewis acid such as zinc chloride and aluminum chloride or a solid acid such as cation exchange resin is used as the catalyst, dehydration is accomplished substantially quantitatively under relatively mild temperature conditions such as not exceeding 200°C. in the absence of a solvent or preferably in the presence of an organic solvent such as a hydrocarbon, a primary alcohol, an ether or a ketone. In case a solid acid, such as alumina, silica-alumina and activated silica is used as the catalyst, in order to accomplish the dehydration in a short reaction time, it is preferred that the reaction be carried out at a relatively high temperature in the range from 150° to 300°C.

When the thus obtained dehydration product is subjected to hydrogenation under the same conditions as described above in [A], squalane is obtained. Squalane is used as an additive or base for the production of various cosmetics due to its advantageous skin-cleaning and penetrating action. It is also valuable as a lubricant in precision equipment.

[C] The method for preparing squalane by hydrogenolysis of the diol [I], a partial hydrogenation product thereof or of 2,6,10,15,19,23-hexamethyltetracosa-10,15-diol is as follows:

The hydrogenolysis to be conducted in the above-mentioned methods (ii), (iii) and (iv) is accomplished at a high temperature by adding an acidic substance generally used for dehydration to an ordinary hydrogenation system.

As the catalyst suitable for this hydrogenolysis, there may be mentioned metals such as nickel, palladium, rhodium and iridium, compounds of these metals, and supported catalysts comprising these metal components supported on suitable carriers. The hydrogenolysis using such catalysts can be conducted according to various methods such as mentioned below.

1. Method Conducted in Organic Carboxylic Acid:

As the carboxylic acid, there are preferably employed acetic acid, propionic acid, butyric acid and isobutyric acid. These carboxylic acids may be used in combination with other carboxylic acids having a high acidity, such as α-halogen fatty acids and α-hydroxy fatty acids.

2. Method Conducted in Inert Organic Solvent in Presence of Acidic Substance:

As the organic solvent, there are preferably employed, for example, saturated hydrocarbons such as hexane, heptane, cyclohexane, ethylcyclohexane, decalin, squalane and crocetane, which is one of the intended products of this invention. When aromatic hydrocarbons, cyclic ethers, esters, ketones, alcohols, especially tertiary alcohols such as tert-butanol, and the like are employed, such side reactions as hydrogenation, ring-opening, hydrolysis and dehydration occur under some reaction conditions. Therefore, it is preferred that these solvents not be used under such conditions.

The following compounds are effectively used as the acidic substance:

a. Brønsted acids such as sulfuric acid, hydrochloric acid, phosphoric acid, perchloric acid, boric acid and the like;

b. Lewis acids such as zinc chloride, aluminum chloride, boron trifluoride and the like;

c. Acidic salts of strong acids and strong bases such as sodium hydrogensulfate, sodium hydrogenphosphate, potassium hydrogensulfate and the like;

d. Salts of strong acids and weak bases such as magnesium sulfate, zinc sulfate, calcium sulfate, copper sulfate, magnesium chloride and the like;

e. Solid acids such as silica-alumina, solid phosphoric acid and the like; and f. Organic carboxylic acids such as acetic acids, formic acid, monochloracetic acid, butyric acid and the like.

In conducting the hydrogenolysis according to the above-mentioned methods, with respect to the combination of a hydrogenation catalyst and an acidic substance or the combination of a hydrogenation catalyst, an acidic substance and a solvent, it is preferred to select a combination such that the hydrogenation catalyst is not poisoned partially by the acidic substance or solvent nor dissolved by the acidic substance or solvent.

In view of the foregoing and in order to use an industrially advantageous catalyst, it is preferred that the hydrogenolysis reaction be conducted according to the following methods:

a. A method in which hydrogenolysis is conducted in the absence of a solvent or in an inert organic solvent by using a supported nickel or palladium catalyst such as nickel supported on diatomaceous earth and palladium supported on active carbon in the co-presence of a salt of a strong acid and a weak base or a solid acid.

b. A method in which hydrogenolysis is conducted in the presence of a palladium catalyst supported on a carrier such as active carbon in an organic carboxylic acid or in mixed solvent of an organic carboxylic acid and an inert organic solvent stable in said organic carboxylic acid.

In conducting hydrogenolysis according to these methods, the reaction can be carried out at an elevated temperature in the liquid phase. In view of the reaction rate, it is preferred that the reaction temperature be at least about 100°C., preferably within a range of 150° to 300°C.

With respect to the hydrogen pressure, the reaction may be performed under atmospheric hydrogen pressure, but in order to increase the reaction rate, it is preferred that the reaction be carried out under an elevated hydrogen pressure. In general, a hydrogen pressure of about 10 to about 100 Kg/cm$^2$ (gauge pressure) is adopted.

The amount of the catalyst used varies depending on the kind of the catalyst actually employed and, in general, the amount of the catalyst can be changed within a range of about 0.1 to about 10% by weight based on the starting compound.

As pointed out in [B] above, when a compound represented by the general formula [II] is directly subjected to hydrogenolysis, cyclization occurs and it sometimes happens that crocetane of a high purity cannot be obtained. However, if suitable reaction conditions are chosen, crocetane of high purity can be obtained even by subjecting a compound of the general formula [II] directly to hydrogenolysis.

Such reaction conditions can be attained by maintaining the hydrogenation rate much higher than the rate of the apparent dehydration. These reaction conditions depend upon the types of hydrogenation catalyst and the acidic substance, the ratio of the hydrogenation catalyst and the acidic substance, and the reaction temperature.

The present invention will now be detailed by reference to the following non-limiting examples.

EXAMPLE 1

100 g of 3,7,11-trimethyl-6,10-dodecadien-1-yn-3-ol was dissolved in 200 ml of benzene, and 10 g of triphenyl phosphine-rhodium chloride RhCl[P(C$_6$H$_5$)$_3$]$_3$ was added to the solution and reaction was conducted under reflux for 3 hours. As a result of gel permeation chromatography (hereinafter abbreviated to "GPC") of the reaction mixture liquid, it was found that the starting compound was substantially consumed and the intended compound was obtained at a selectivity of 98%.

The solvent was removed from the reaction mixture under reduced pressure and the residue was subjected to thin layer chromatography (using chloroform as a developing solvent). As a result, two small spots and one large spot were observed. Then 20 g of the residue was purified according to column chromatography using 400 g of silica gel (developing solvent = 1:1 mixed solvent of benzene : chloroform), to obtain 15.7 g of a yellow, highly viscous liquid. From the results of mass spectrum analysis, infrared absorption spectrum analysis, elementary analysis and nuclear magnetic resonance spectrum analysis of the liquid, it was identified as 2,6,10,15,19,23-hexamethyl-2,6,11,18,22-tetracosapentaen-13-yne-10,15-diol. Elementary Analysis Values:

Found: C = 81.52%, H = 11.31%, O = 7.65%
Calculated: C = 81.76%, H = 10.97%, O = 7.26%

10 g of the thus obtained 2,6,10,15,19,23-hexamethyl-2,6,11,18,22-tetracosapentaen-13-yne-10,15-diol was dissolved in 50 ml of n-hexane, and 1.0 g of 5% palladium-carbon powder was added to the solution. Hydrogenation was conducted at room temperature under a hydrogen pressure of 100 to 80 Kg/cm$^2$ until absorption of hydrogen was not observed. After completion of the reaction, the catalyst was separated by filtration, and the solvent was removed from the filtrate under reduced pressure to obtain a light yellow, viscous liquid. The liquid was distilled under reduced pressure to obtain 8.3 g of a fraction boiling at 218° to 220°C. under 0.2 mm Hg.

From the results of NMR analysis (proton and C$^{13}$), infrared absorption spectrum analysis, mass spectrum analysis and elementary analysis, the obtained substance was identified as 2,6,10,15,19,23-hexamethyl-tetracosa-10,15-diol.

The ascription of peaks observed in C$^{13}$ NMR spectrum in carbon tetrachloride is as shown below. Each value is based on tetramethylsilane and expressed in the unit of ppm.

① → 23.1
② → 28.2
③ → 23.1
④ → 39.7
⑤ → 25.2
⑥ → 38.2
⑦ → 33.2
⑧ → 20.2
⑨ → 37.7
⑩ → 21.8
⑪ → 42.8
⑫ → 72.1
⑬ → 27.4
⑭ → 42.2
⑮ → 25.2

When 2,6,10,15,19,23-hexamethyl-2,6,11,18,22-tetracosapentaen-13-yne-10,15-diol obtained by the above coupling reaction is subjected to hydrogenolysis in acetic acid in the presence of a Pd/C catalyst the product obtained was found by gas chromatography, nuclear magnetic resonance spectrum and mass spectrum analysis, to be the same as analyzed commercially available squalane. From this fact, it was indirectly confirmed that the above identification was correct.

EXAMPLES 2 to 12

Experimental results shown in Table 1 were obtained by conducting the reaction in the same manner as described above while changing the amount of the catalyst and the kind of the solvent as shown in Table 1. In each example, determination was conducted according to GPC using 2,6,10,15,19,23-hexamethyl-2,6,11,18,22-tetracosapentaen-13-10,15,19,23-hexamethyl-2,6,11,18,22-tetracosapentaen-13-yne-diol obtained in Example 1 and n-decyl alcohol as an internal standard.

The starting alcohol used was 3,7,11-trimethyl-6,10-dodecadien-1-yn-3-ol in each example.

1,6,13,18,23-pentaene-10,15-diol. Results of elementary analysis of the so obtained substance were as follows:

Found: C = 82.01%, H = 10.33%, 0 = 6.97%
Calculated: C = 81.76%, H = 10.97%, 0 = 7.26%

TABLE 1

| Example No. | Amount (g) of Starting Alcohol | Amount (g) of RHCl[(C₆H₅)₃P]₃ | Solvent | Reaction Conditions | Yield (%) of Diol |
|---|---|---|---|---|---|
| 2 | 10 | 1.0 | 20 ml of C₆H₆ | reflux, 1 hour | 88 |
| 3 | 10 | 1.0 | " | reflux, 3 hours | 98 |
| 4 | 10 | 0.5 | " | reflux, 1 hour | 48 |
| 5 | 10 | 0.5 | " | reflux, 3 hours | 54 |
| 6 | 10 | 0.5 | " | reflux, 7 hours | 70 |
| 7 | 10 | 0.2 | " | reflux, 3 hours | 12 |
| 8 | 10 | 0.5 | 20 ml of EtOH | reflux, 1 hour | 15 |
| 9 | 10 | 0.2 | " | reflux, 1 hour | 6 |
| 10 | 10 | 0.5 | 20 ml of CH₃C₆H₅ | reflux, 1 hour | 75 |
| 11 | 10 | 0.5 | 20 ml of (CH₃)₂C₆H₄ | reflux, 1 hour | 81 |
| 12 | 10 | 0.2 | " | reflux, 1 hour | 20 |

EXAMPLE 13

1.0 g of deep blue triphenyl phosphine-cobalt chloride complex CoCl$_2$[P(C$_6$H$_5$)$_3$]$_2$ obtained according to the method reported by F. A. Cotton et al in *J. Amer. Chem. Soc.*, 83, 1780–1785 (1961) was added to a solution of 5 g of 3,7,11-trimethyl-6,10-dodecadien-1-yn-3-ol in 20 ml of benzene, and the reaction was conducted under reflux in a nitrogen gas current for 3 hours. From the results of GPC of the reaction mixture liquid, it was found that the conversion of the starting compound was 62% and the selectivity for 2,6,10,15,19,23-hexamethyl-2,6,11,18,22-tetracosapentaen-13-yne-10,15-diol was 96%.

EXAMPLE 14

1.0 g of deep blue triphenyl phosphine-nickel chloride NiCl$_2$[P(C$_6$H$_5$)$_3$]$_2$ obtained according to the method reported by L. M. Venanzi in *J. Chem. Soc.*, 719–724 (1958) was added to a solution of 5 g of 3,7,11-trimethyl-6,10-dodecadien-1-yn-3-ol in 20 ml of benzene, and the reaction was conducted under reflux in a nitrogen gas current for 3 hours. From the results of PGC of the reaction mixture liquid it was found that the conversion of the starting compound was 34% and the selectivity for the desired product was 93%.

EXAMPLE 15

In the same manner as described in Example 13, the reaction was conducted by adding 20% by weight of triphenyl phosphine-palladium chloride complex PdCl$_2$[P(C$_6$H$_5$)$_3$]$_2$ to 3,7,11-trimethyl-6,10-dodecadien-1-yn-3-ol. The conversion of the starting compound was 52% and the selectivity to the product was 96%.

EXAMPLE 16

The reaction and post-treatment were conducted in the manner as described in Example 1 by using 110 g of 3,7,11-trimethyldodeca-1-yne-6,11-dien-3-ol as the starting compound and 10.0 g of triphenyl phosphine-rhodium chloride complex RhCl[P(C$_6$H$_5$)$_3$]$_3$, to obtain 118 g of a crude product. Then, 10 g of the crude product was purified by silica gel column chromatography to obtain 8.4 g of a yellow liquid. From the results of nuclear magnetic resonance spectrum analysis, infrared absorption spectrum analysis and mass spectrum analysis, the so obtained substance was identified as 2,6,10,15,19,23-hexamethyltetracosa-11-yne- When the above crude product was analyzed according to GPC using same as a standard, it was found that the crude product contained 94.8% of 2,6,10,15,19,23-hexamethyltetracosa-11-yne-1,6,13,18,23-pentaene-10,15-diol. 80 g of this crude product was hydrogenated in the presence of a Pd/C catalyst under the same conditions as in Example 1 and the hydrogenation product was distilled in vacuo to obtain 70.2 g of a fraction boiling at 214° to 216°C. under 0.15 mm Hg.

From the results of nuclear magnetic resonance spectrum analysis (proton and C$^{13}$), mass spectrum analysis and gas chromatography analysis, it was found that the so recovered product was 2,6,10,15,19,23-hexamethyltetracosa-10,15-diol.

EXAMPLE 17

38.8 g of geranyl acetone was dissolved in 100 ml of n-hexane, and hydrogenation was conducted in the presence of 1.9 g of a 5% Pd/carbon catalyst at room temperature under atmospheric pressure. The catalyst was separated and the solvent was then distilled under reduced pressure to obtain 39.1 g of tetrahydrogeranyl acetone.

The so obtained crude product was reacted with acetylene in liquid ammonia directly without purification, to thereby effect ethynylation. Liquid ammonia was removed from the reaction mixture liquid and the residue was neutralized with ammonia chloride. The neutralization product was thrown into water and extracted with ether.

The ether extract was dried with Glauber's salt and ether was removed. The residue was distilled under high vacuum to obtain 41.5 g of 3,7,11-trimethyl-dodeca-1-yn-3-ol in the form of a fraction boiling at 133° to 136°C. under 5 mm Hg.

The so obtained product was dissolved in 300 ml of benzene, and 3.7 g of tris-(tricyclohexylphosphine)-rhodium complex Rh[P(C$_6$H$_{11}$)$_3$]$_3$ was added to the solution. The reaction was conducted under reflux for 4 hours in a nitrogen gas atmosphere.

After completion of the reaction, the reaction mixture liquid was passed through a chromatograph column packed with silica gel and having an inner diameter of 10 cm and a length of 30 cm to separate the catalyst from the reaction product. The solvent was distilled from the effluent under reduced pressure to obtain 36.7 g of 2,6,10,15,19,23-hexamethyltetracosa- 11-yn-13-ene-10,15-diol in the form of a red viscous liquid.

The obtained compound was hydrogenated by using 5 g of 5% palladium/carbon under atmospheric pressure at 50°C. and when hydrogen was sufficiently absorbed, the reaction was stopped. The catalyst was separated and the solvent was distilled to obtain 36.4 g of 2,6,10,15,19,23-hexamethyltetracosa-10,15-diol in the form of a light yellow liquid.

The thus obtained diol was dissolved in 300 ml of benzene and 0.2 g of p-toluenesulfonic acid was added to the solution as a catalyst. Dehydration was conducted under heat and reflux while removing water formed by the reaction from the reaction system.

The reaction mixture liquid was neutralized, washed with water and dried with Glauber's salt. The solvent was distilled off and the residue was subjected to infrared absorption spectrum analysis. Completion of the dehydration reaction was confirmed from the fact that the absorption of the hydroxyl group at 3300 to 3500 $cm^{-1}$ disappeared and the absorption of the double bond appeared in the vicinity of 1660 $cm^{-1}$. 30.7 g of the obtained dehydration product was dissolved in 100 ml of n-hexane, and hydrogenation was conducted at room temperature under atmospheric pressure in the presence of 3.0 g of a 5% palladium/carbon catalyst. The catalyst was separated and the solvent was distilled to obtain 29.8 g of squalane in the form of a colorless flowable liquid.

EXAMPLES 18 to 25

154 g of commercially available citronellal (3,7-dimethyl-6-octenol) was reacted in 500 ml of acetone in the presence of 80 g of 55% NaOH at 60°C. for 4 hours. The reaction mixture liquid was thrown into water, extracted with ether, washed with water and dried with Glauber's salt, and the solvent was distilled to obtain 148 g of citronellydene-acetone-(3,7-dimethyl-3,9-undecadien-2-one).

The obtained compound was hydrogenated in 500 ml of n-hexane in the presence of 5 g of a 5% palladium/-carbon catalyst. The catalyst was separated and the solvent was distilled to obtain 146.2 g of 3,7-dimethyl-9-undecen-2-one. The resultant compound was then reacted with acetylene in liquid ammonia to obtain 150.3 g of 3,7,11-trimethyl-1-yn-10-en-3-ol.

The alkynol obtained was dissolved in 500 ml of benzene and 15 g of tris-(tri-n-butylphosphine)-rhodium chloride complex $RhCl[P(n-Bu)_3]_3$ was added to the solution. The mixture was heated and refluxed for 5 hours.

The reaction mixture liquid was passed through a chromatograph column having an inner diameter of 15 cm and a length of 50 cm packed with diatomaceous earth to separate the catalyst from the reaction mixture. Then, the solvent was distilled to obtain 137.8 g of 2,6,10,15,19,23-hexamethyltetracosa-2,13,22-trien-11-yne-10,15-diol in the form of a dark red viscous liquid.

Hydrogenolysis of the resultant compound was conducted while changing the reaction conditions as shown in Table 2, to obtain results shown in Table 2.

In this hydrogenolysis reaction, the above diol was used in the form of a 10% solution in n-heptane.

Table 2

| Example No. | Amount (g) of Diol | Catalyst | Reaction Conditions | Yield (%) of Squalane |
|---|---|---|---|---|
| 18 | 10 | 0.21 g of diatomaceous earth and 0.42 g of silica-alumina | 230°C., 1.5 hours, $H_2$ pressure of 110–112 $Kg/cm^2$ | 95.7 |
| 19 | 10 | 0.21 g of diatomaceous earth and 0.62 g of silica-alumina | 230°C., 2 hours, $H_2$ pressure of 100–112 $Kg/cm^2$ | 98.9 |
| 20 | 10 | 0.40 g of Ni-diatomaceous earth and 0.20 g of silica-alumina | 230°C., 1 hour, $H_2$ pressure of 90–98 $Kg/cm^2$ | 91.4 |
| 21 | 10 | 0.17 g of Ni-diatomaceous earth and 0.33 g of silica-alumina | 180–210°C., 2 hours, $H_2$ pressure of 92–105 $Kg/cm^2$ | 90.6 |
| 22 | 20 | 0.17 g of Ni-diatomaceous earth and 0.34 g of silica-alumina | 180–200°C., 2 hours, $H_2$ pressure of 92–105 $Kg/cm^2$ | 98.8 |
| 23 | 20 | 0.21 g of Ni-diatomaceous earth and 0.42 g of silica-alumina | 230°C., 0.5 hour, $H_2$ pressure of 72–82 $kg/cm^2$ | 97.7 |
| 24 | 20 | 0.21 g of Ni-diatomaceous earth and 0.42 g of silica-alumina | 230°C., 1 hour, $H_2$ pressure of 105 $Kg/cm^2$ | 96.8 |
| 25 | 20 | 0.21 g of Ni-diatomaceous earth and 0.62 g of silica-alumina | 210–230°C., 1 hour, $H_2$ pressure of 110–120 $Kg/cm^2$ | 98.2 |

While the invention has been described and illustrated with reference to certain preferred embodiments thereof, those skilled in the art will appreciate that various changes, modifications and substitutions therein can be made without departing from the spirit of the invention. It is intended, therefore, that the invention be limited only by the scope of the claims which follow.

What is claimed is:

1. A diol represented by the following general formula [I]:

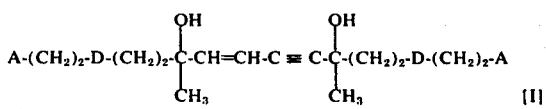

wherein A is

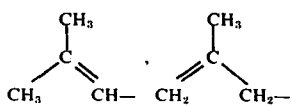

or

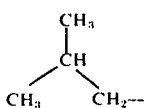

D is

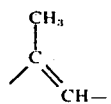

or

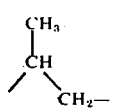

and wherein A— groups may be the same or different and the —D— groups may be the same or different.

2. The diol as defined by claim 1, wherein said diol comprises 2,6,10,15,19,23-hexamethyltetracosa-11-yne-E-10,15-diol and E is mono-, di-, tri-, tetra- or penta-ene.

3. The diol as defined by claim 1, wherin said diol is selected from the group consisting of 2,6,10,15,19,23-hexamethyltetracosa-11-yne-2,6,13,18,22-pentaene-10,15-diol, 2,6,10,15,19,23-hexamethyltetracosa-11-yne-2,13,22-triene-10,15-diol, 2,6,10,15,19,23-hexamethyltetracosa-11-yne-1,6,13,18,23-pentaene-10,15-diol, 2,6,10,15,19,23-hexamethyltetracosa-11-yne-1,13,23-triene-10,15-diol, 2,6,10,15,19,23-hexamethyltetracosa-11-yne-6,13,18-triene-10,15-diol and 2,6,10,15,19,23-hexamethyltetracosa-11-yn-13-ene-10,15-diol.

* * * * *

UNITED STATES PATENT OFFICE
CERTIFICATE OF CORRECTION

PATENT NO. : 3,975,451
DATED : August 17, 1976
INVENTOR(S) : YOSHIJI FUJITA et al It is certified that error appears in the above-identified patent and that said Letters Patent are hereby corrected as shown below:

IN THE ABSTRACT OF THE DISCLOSURE:

Line 3, "Group VII" should read -- Group VIII --.

Signed and Sealed this

Fifteenth Day of February 1977

[SEAL]

Attest:

RUTH C. MASON
*Attesting Officer*

C. MARSHALL DANN
*Commissioner of Patents and Trademarks*